United States Patent [19]
Hussain

[11] Patent Number: 6,063,852
[45] Date of Patent: May 16, 2000

[54] BROMINATED POLYPHENYLMETHANES, PROCESS FOR THEIR PREPARATION AND FIRE RETARDANT COMPOSITIONS CONTAINING THEM

[75] Inventor: Saadat Hussain, Baton Rouge, La.

[73] Assignee: Albermarle Corporation, Richmond, Va.

[21] Appl. No.: 09/090,502

[22] Filed: Jun. 4, 1998

[51] Int. Cl.[7] .............................. C08K 5/02; C08G 61/00; C07C 22/00
[52] U.S. Cl. ..................... 524/464; 524/469; 528/397; 570/185; 570/206; 570/231
[58] Field of Search ...................... 524/464, 469; 528/397; 570/185, 206, 231

[56] References Cited

U.S. PATENT DOCUMENTS

| | | | |
|---|---|---|---|
| 2,477,978 | 8/1949 | Graenacher et al. | 570/185 |
| 2,602,823 | 7/1952 | Ross et al. | 570/185 |
| 2,830,096 | 4/1958 | Lane | 570/185 |

*Primary Examiner*—Kriellion Sanders
*Attorney, Agent, or Firm*—E. E. Spielman, Jr.

[57] ABSTRACT

Novel brominated polyphenylmethanes, such as poly (tetrabromobenzyl bromide), are provided in a one step process by reacting a benzyl halide and bromine in the presence of a Friedel Crafts catalyst. The brominated polyphenylmethanes can be added to flammable organic polymers to make flame retardant polymer compositions.

15 Claims, No Drawings

BROMINATED POLYPHENYLMETHANES, PROCESS FOR THEIR PREPARATION AND FIRE RETARDANT COMPOSITIONS CONTAINING THEM

TECHNICAL FIELD

This invention relates generally to the preparation of bromine containing polymers which are useful as flame retardants in plastic compositions and, more specifically, to brominated polyphenylmethanes which can be formed by a one-step procedure in which benzyl halides are both polymerized and brominated by reacting the benzyl halide, such as benzyl bromide, with bromine in the presence of a Friedel Crafts catalyst.

BACKGROUND

Ring-bromination of toluene using small amounts (10–20 mole %) of transition metal halide catalysts has been used to prepare monomeric flame retardants for polymers such as ABS resins and polypropylene. While attempting to ring-brominate benzyl bromide using a $AlCl_3$ catalyst in bromine, it was unexpectedly found that the primary product was a novel, ring-brominated polymer, poly(tetrabromobenzylbromide). Polymeric flame retardants have several desirable properties such as non-blooming character and generally good UV stability, which is not always the case with monomeric flame retardants.

SUMMARY OF INVENTION

In accordance with this invention there is provided brominated polyphenylmethane.

Also provided is a process for preparing a brominated polyphenylmethane comprising reacting a benzyl halide with bromine in the presence of from about 0.001 to 0.5 mole of Friedel Crafts catalyst per mole of benzyl halide so as to ring brominate and polymerize the benzyl halide to form brominated polyphenylmethane.

Furthermore, there is provided a flame retardant polymer composition comprising a flammable organic polymer and a flame retardant amount of brominated polyphenylmethane.

Examples of benzyl halides which can be brominated and polymerized to form the brominated polyphenylmethane polymers of the invention include benzyl bromide, benzyl chloride and ring substituted benzyl chlorides and bromides which contain one or two substituents such as hydrocarbon and substituted hydrocarbon groups and halogens, including combinations thereof. For example, Br, Cl, and alkyl and aryl groups, i.e., methyl, phenyl, halomethyl, and the like.

It is preferred to employ bromine as the only solvent medium for the reaction. However, from about 10 to 200 volume percent based on the total volume of reaction mixture, of inert organic solvents such as halogenated, saturated aliphatic hydrocarbons can also be included. For example, carbon tetrachloride, chloroform, tetrachlorethane, methylene chloride, dibromoethane, and the like.

It is preferred that the bromine used in the process of this invention be essentially anhydrous, i.e., contain less than 100 ppm water, and contain no more than 10 ppm by weight of organic impurities, e.g., oil, grease, carbonyl containing hydrocarbons, iron, and the like. With such a bromine purity, there is little, if any, impact on the color attributes of the polybrominated product. Available, commercial grade bromine may have such purity. If, however, such is not available, the organic impurities and water content of the bromine can be conveniently reduced by mixing together a 3 to 1 volume ratio of bromine and concentrated (94–98 percent) sulfuiric acid. A two-phase mix is formed which is stirred for 4 to 8 hours. After stirring and settling, the sulfuric acid phase, along with the impurities and water, is separated from the bromine phase. To further enhance the purity of the bromine, the recovered bromine phase can be subjected to distillation.

Preferably, an excess (10% or more) over the stoichiometric amount of bromine needed to completely ring brominate the empty sites on the benzyl halide is used. More preferably, when bromine is the only solvent medium for the reaction, from about a 50 to 100% stoichiometric excess is used. Larger amounts could be used, but are not needed and just increase the cost.

Non-limiting examples of suitable Friedel Crafts catalysts for use in the process of the invention include $AlCl_3$, $FeBr_3$, $AlBr_3$, $SbCl_3$, $SbCl_5$, $SnCl_2$, $SnCl_4$, $ZnCl_2$, $ZrCl_4$, $TiCl_4$, $TeCl_2$, $BrCl_3$ and $CdCl_2$. The amount of catalyst used in the process of the invention is from about 0.001 to 0.5, and preferably from about 0.01 to 0.2, mole per mole of benzyl halide. This amount is much less than the amount required to conduct the usual Friedel Crafts alkylation reaction, where a molar equivalent amount of catalyst and alkyl halide is generally used.

The reactants and catalyst can be mixed in any order. Preferably, the benzyl halide is added to a mixture of the catalyst and bromine and the reaction mixture is then heated and stirred at reflux for several hours. After cooling, water is added to decompose the catalyst and the excess bromine is distilled off to leave a solid, polymeric product.

The process both ring brominates the empty sites on the benzyl halide and polymerizes the brominated benzyl halide by an alkylation reaction so as to produce polyphenylmethanes having the general formula:

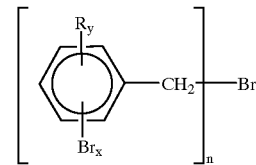

Where x is 1 to 4 on each ring except for one end ring where x is 1–5, y is 0 to 2, each R is, independently, halogen, hydrocarbon or substituted hydrocarbon containing from 1 to about 20 carbons, and n averages from about 5 to 100 (preferably, from about 10 to 50).

When each ring is completely brominated, the product is referred to in this specification as poly(tetrabromobenzyl bromide) in which each repeating unit of the product polymer contains 4 bromines and each end group will have 5 bromine atoms. This definition is not intended to delineate any particular mechanism for the polymerization reaction.

It is expected that the brominated polyphenylmethane polymers could also be made by either polymerizing pentabromobenzyl halides or by brominating polyphenylmethanes.

The brominated polyphenylmethane products can be used as flame retardant additives in polymers such as, for example, ABS resins, polystyrenes, polypropylenes, polyamides and polyesters. The brominated polyphenylmethanes are usually used in flame retardant amounts of from about 3 to 25% by weight based on the total weight of polymer composition. Ignition resistant compounds which improve the flame retardant properties of the compositions can also be included. For example, antimony, phosphorus and boron containing compounds. Non-limiting specific examples of such compounds include antimony trioxide ($Sb_2O_3$), triphenyl stilbene, trialkoxy stilbene, phosphorous tribromide, phosphorous trichloride, phosphorous oxychloride, triphenyl phosphate, triethyl phosphate, trialkyl borate, and the like. A preferred compound is antimony trioxide. The ignition resistant compounds are usually used in amounts of from about 0.5 to 10% by weight based on the total weight of polymer composition. Both the flame retardant polymers of the invention and the ignition resistant compounds can be incorporated into a small amount of the host polymer to form a masterbatch formulation which contains 10 to 50% by weight or more of the additives. The masterbatch is then blended with the bulk of the host polymer in amounts to provide the desired percentages of bromine and ignition resistant compound in the finished polymer composition.

The invention is further illustrated by, but is not intended to be limited to, the following examples.

EXAMPLE I

| Ingredients | Moles | Mol. Wt. | Grams |
|---|---|---|---|
| Benzyl bromide (Aldrich, 98%) | 0.1 | 171.04 | 17.1 |
| Bromine (Aldrich, 99.5+% pure, 100% stoichiometric excess) | 1.0 | 159.82 | 160.0 |
| $AlCl_3$ (anhydrous, 10% by wt. of the benzyl bromide) | 0.0127 | 133.34 | 1.7 |

Procedure

A 500 mL resin kettle equipped with a mechanical stirrer, a thermometer with a temperature regulator, an addition funnel, a reflux condenser attached to a tubing to carry exhaust gases to a caustic scrubber, and a heating mantle, is charged with bromine (160 g, 51.6 mL), and aluminum chloride (anhydrous, 1.7 g). The amount of bromine is a 100% excess over the stoichiometric amount needed to completely ring brorninate the empty sites on the benzyl bromide. The slurry is stirred at 25° C. while benzyl bromide (17.1 g, charged previously into the addition funnel) is added dropwise to the stirred bromine/aluminum chloride slurry over a period of twenty-five minutes. The reaction mixture is now heated and stirred at reflux (60° C.) for four hours and then cooled to about 45° C. Water (150 mL) is then charged to the reactor to decompose the catalyst and the excess bromine is distilled (22 mL collected). The resulting solid is removed from the kettle and crushed. The product is then washed with water and dried in air overnight, to give 49 g (86.6%) of a brown powder which melts over a wide range, starting at 150° C. The crude product is stirred with toluene (400 mL) at reflux (105° C.) and the resulting slurry is filtered, while hot, through a filter paper. Most of the product is found on the filter paper, and cooling of the filtrate does not give any further precipitation. The filter cake is allowed to dry. This product decomposes at 444–450° C. without melting. Intermolecular alkylation along with bromination apparently occurs so as to produce a solid, brominated polyphenylmethane product. By changing the amount of bromine used, the catalyst amount and type, and the reaction conditions( e.g., use of a solvent), polymers having specific desired characteristics can be obtained.

EXAMPLE II

The product according to Example 1 can be formulated with an ABS resin in an amount of about 18% by weight of total polymer composition along with about 4% by weight of total polymer composition of antimony oxide so as to provide a flame retardant ABS resin based polymer composition.

What is claimed is:
1. Brominated polyphenylmethane.
2. Brominated poly(benzyl halide).
3. Brominated poly(benzyl bromide).
4. The product of claim 2 having the general formula:

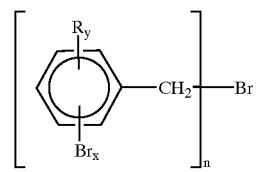

Where x is 1–4 except for one end ring where x is 1–5, y is 0 to 2, each R is, independently, halogen, hydrocarbon or substituted hydrocarbon containing from about 1 to 20 carbons, and n has an average of from about 5to 100.
5. Poly(tetrabromobenzyl bromide).
6. A process for preparing a brominated polyphenylmethane comprising reacting a benzyl halide with bromine in the presence of from about 0.001 to 0.5 mole of a Friedel Crafts catalyst per mole of benzyl halide so as to ring brominate and polymerize the benzyl halide to form brominated polyphenylmethane.
7. The process of claim 6 wherein at least about a 10% excess over the stoichiometric amount of bromine needed to completely ring brominate the empty sites on the benzyl halide is present.
8. The process of claim 6 wherein the amount of catalyst is from about 0.01 to 0.2 mole per mole of benzyl halide.
9. The process of claim 6 wherein the benzyl halide is benzyl bromide.
10. The process of claim 9 wherein the brominated polyphenylmethane has the general formula:

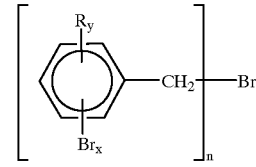

Where x is 1–4 except for one end ring where x is 1–5, y is 0 to 2, each R is, independently, halogen, hydrocarbon or substituted hydrocarbon containing from about 1 to 20 carbons, and n has an average of from about 5 to 100.
11. The process of claim 9 wherein the product is poly (tetrabromobenzyl bromide).
12. A flame retardant polymer composition comprising a flammable organic polymer and a flame retardant amount of a brominated polyphenylmethane.
13. The composition of claim 12 wherein said flammable organic polymer is selected from the group consisting of ABS resins, polystyrenes, polypropylenes, polyamides and polyesters.
14. The composition of claim 13 wherein said brominated polyphenylmethane has the general formula:

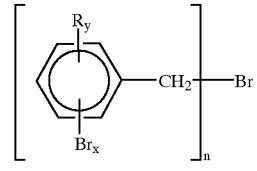

Where x is 1–4 except for one end ring where x is 1–5, y is 0 to 2, each R is, independently, halogen, hydrocarbon or substituted hydrocarbon containing from about 1 to 20 carbons, and n has an average of from about 5 to 100.
15. The composition of claim 12 wherein said brominated polyphenylmethane is poly(tetrabromobenzyl bromide).

* * * * *